(12) United States Patent
Shiroishi et al.

(10) Patent No.: US 10,210,611 B2
(45) Date of Patent: Feb. 19, 2019

(54) IMAGE PROCESSING APPARATUS, IMAGE PROCESSING METHOD, AND COMPUTER PROGRAM PRODUCT

(71) Applicant: Toshiba Medical Systems Corporation, Otawara-shi (JP)

(72) Inventors: Ryo Shiroishi, Nasushiobara (JP); Tomohiro Kawasaki, Otawara (JP); Yasuko Fujisawa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 78 days.

(21) Appl. No.: 15/395,362

(22) Filed: Dec. 30, 2016

(65) Prior Publication Data

US 2017/0206654 A1 Jul. 20, 2017

(30) Foreign Application Priority Data

Jan. 14, 2016 (JP) ................................. 2016-005182

(51) Int. Cl.
*G06T 7/00* (2017.01)
*G16H 50/50* (2018.01)
*G06F 19/00* (2018.01)

(52) U.S. Cl.
CPC ............ *G06T 7/0012* (2013.01); *G06F 19/00* (2013.01); *G06T 7/0016* (2013.01); *G16H 50/50* (2018.01);
(Continued)

(58) Field of Classification Search
CPC ............... G16H 50/50; G06T 2200/04; G06T 2207/30016; G06T 2207/10088
See application file for complete search history.

(56) References Cited

U.S. PATENT DOCUMENTS

2009/0005693 A1   1/2009   Brauner et al.
2011/0130675 A1*  6/2011   Bibian ................. A61B 5/0476
                                             600/544
(Continued)

FOREIGN PATENT DOCUMENTS

JP      2014-526339      10/2014
JP      2015-91432       5/2015

OTHER PUBLICATIONS

Shannon L. Risacher, et al., "Neuroimaging and Other Biomarkers for Alzheimer's Disease: The Changing Landscape of Early Detection", Annu Rev Clin Psychol. 2013; Doi:10.1146/annurev-clinpsy-050212-185535., 31 pages.

*Primary Examiner* — Qian Yang
(74) *Attorney, Agent, or Firm* — Oblon, McClelland, Maier & Neustadt, L.L.P.

(57) ABSTRACT

An image processing apparatus according to an embodiment includes processing circuitry. The processing circuitry is configured to obtain a value of an index related to a predetermined disease for each of a plurality of sites included in a brain of a patient, on the basis of a plurality of pieces of medical image data obtained by imaging the brain of the patient at each of a plurality of points in time. The processing circuitry is configured to analyze, for each of the plurality of sites, a relationship between changes in the value at the plurality of points in time and a progress model indicating changes in the index through progress of the predetermined disease. The processing circuitry is configured to output an analysis result obtained from the analysis for each of the plurality of sites.

10 Claims, 12 Drawing Sheets

(52) U.S. Cl.
CPC ............... *G06T 2200/04* (2013.01); *G06T 2207/10088* (2013.01); *G06T 2207/30016* (2013.01)

(56) References Cited

U.S. PATENT DOCUMENTS

2012/0070044 A1* 3/2012 Avinash ............... G06K 9/3233
382/128
2014/0303487 A1 10/2014 James et al.

\* cited by examiner

FIG.7
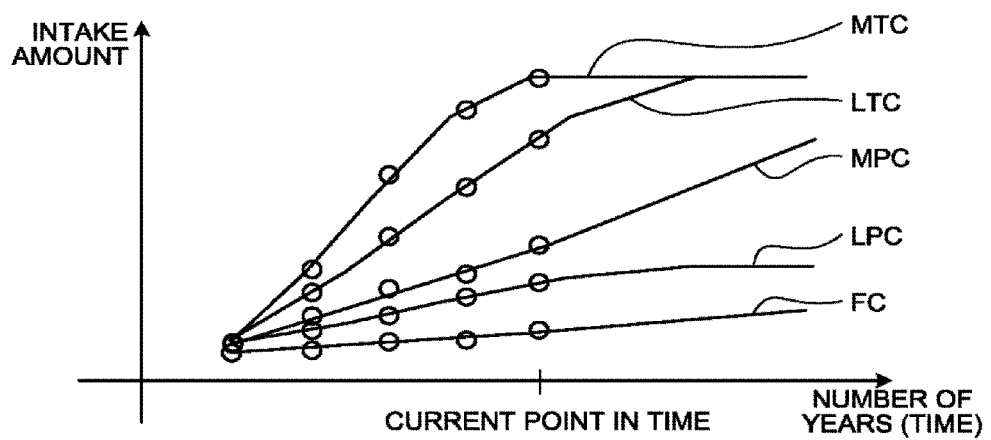
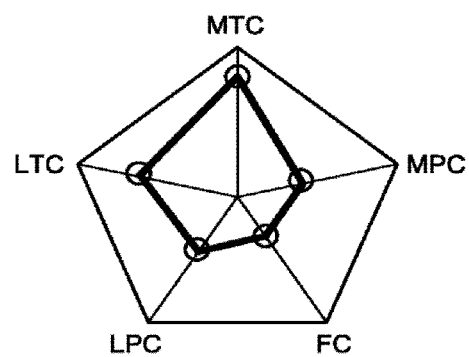

IMAGE PROCESSING APPARATUS, IMAGE PROCESSING METHOD, AND COMPUTER PROGRAM PRODUCT

CROSS-REFERENCE TO RELATED APPLICATIONS

This application is based upon and claims the benefit of priority from Japanese Patent Application No. 2016-005182, filed on Jan. 14, 2016; the entire contents of which are incorporated herein by reference.

FIELD

Embodiments described herein relate generally to an image processing apparatus, an image processing method, and a computer program product.

BACKGROUND

Conventionally, to diagnose or to predict into the future a degree of progress of diseases, analyses are performed by using medical images. For example, to diagnose Alzheimer's disease (Alzheimer-type dementia), atrophy of the brain caused by progress of the disease is evaluated by performing an analysis while using images acquired with Magnetic Resonance Imaging (MRI). More specifically, according to a known technique for evaluating atrophy of the brain, the region of the brain is detected from an MRI image obtained by imaging the head of an examined subject (hereinafter "patient"), and the volume of the detected brain is measured. Further, for example, according to a known technique (called Voxel-based Morphology) for evaluating the degree of atrophy, an image of the brain of a patient is positioned so as to be aligned with a standard image of the brain (a standard brain). However, to perform these types of analyses accurately, it is necessary to detect the brain and align the position thereof in a precise manner.

BRIEF DESCRIPTION OF THE DRAWINGS

FIG. 7 is a drawing for explaining a first display example resulting from a process performed by a display controlling function according to the first embodiment;

DETAILED DESCRIPTION

An image processing apparatus according to an embodiment includes processing circuitry. The processing circuitry is configured to obtain a value of an index related to a predetermined disease for each of a plurality of sites included in a brain of a patient, on the basis of a plurality of pieces of medical image data obtained by imaging the brain of the patient at each of a plurality of points in time. The processing circuitry is configured to analyze, for each of the plurality of sites, a relationship between changes in the value at the plurality of points in time and a progress model indicating changes in the index through progress of the predetermined disease. The processing circuitry is configured to output an analysis result obtained from the analysis for each of the plurality of sites.

Exemplary embodiments of an image processing apparatus, an image processing method, and a computer program product will be explained, with reference to the accompanying drawings.

An image processing apparatus 100 according to an embodiment makes it possible to easily perform an analysis on progress of a disease, by obtaining index values in a time series for each of a plurality of sites and displaying a relationship between changes in the obtained index values and a progress model. In the present example, the progress model indicates changes in each of the indexes through progress of a predetermined disease.

For example, with Alzheimer's disease (Alzheimer-type dementia), which is one of neurodegenerative diseases, partial neurodegeneration occurs in the brain and gradually spreads in the course of the progress of the disease. The neurodegeneration is observed as atrophy (a decrease in the volume) or degradation of metabolic capacity in images taken by performing, for example, a Magnetic Resonance Imaging (MRI) examination, a Positron Emission computed Tomography (PET) examination, a Single Photon Emission Computed Tomography (SPECT) examination or the like. Accordingly, the image processing apparatus 100 according to the present embodiment is configured to use the volume of the brain and a metabolic capability level obtained from these types of images as indexes and to further analyze and display a relationship between chronological changes in each of the indexes and a progress model. In other words, the image processing apparatus 100 according to the present embodiment makes it possible to easily assess an onset or stages (degrees of progress) of the disease, by comparing the temporal/spatial (positional) changes in each of the indexes with the progress model.

In the following sections, an example will be explained in which an analysis related to progress of Alzheimer's disease is performed. However, possible embodiments are not limited to this example. The present disclosure is widely applicable to analyses of other diseases.

First Embodiment

Figure 1:
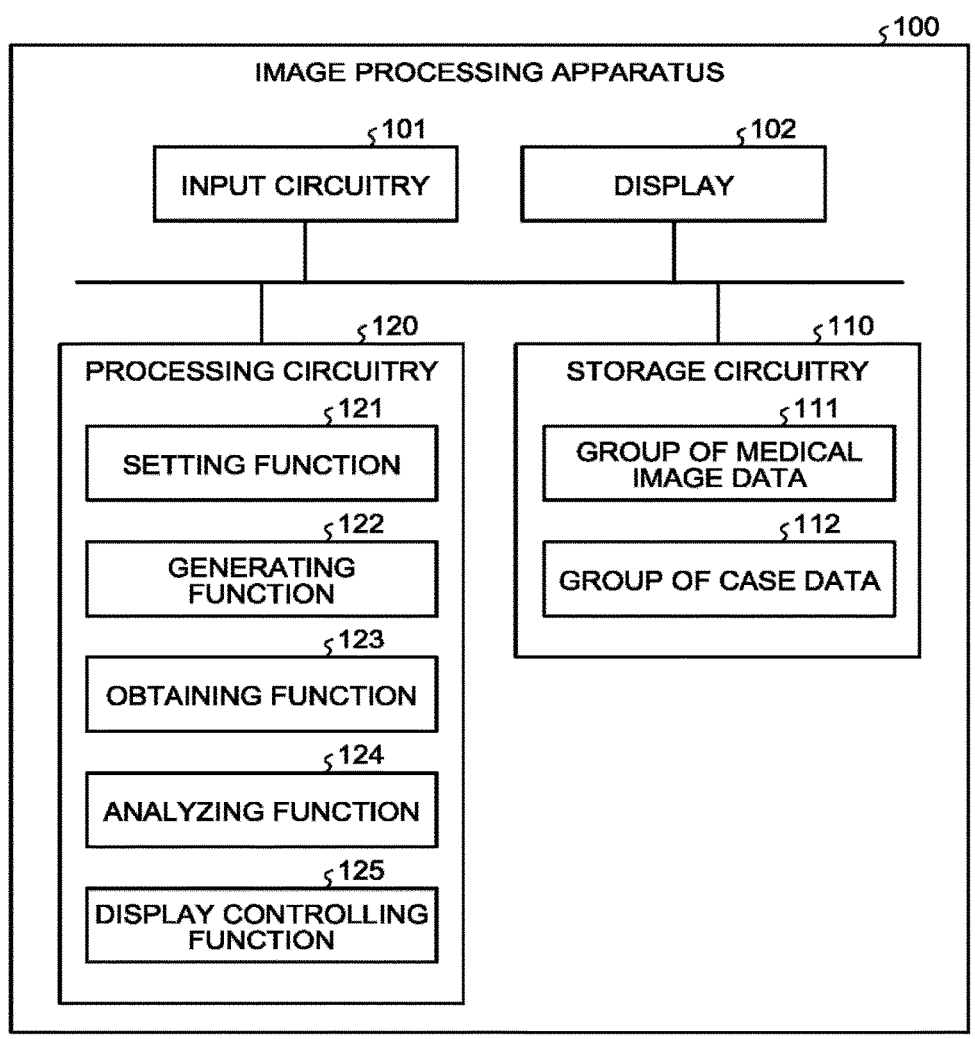
FIG. 1 is a block diagram illustrating an exemplary configuration of an image processing apparatus according to a first embodiment.

FIG. 1 is a block diagram illustrating an exemplary configuration of the image processing apparatus 100 according to the first embodiment. As illustrated in FIG. 1, for example, the image processing apparatus 100 according to the first embodiment includes input circuitry 101, a display 102, storage circuitry 110, and processing circuitry 120. The input circuitry 101, the display 102, the storage circuitry 110, and the processing circuitry 120 are connected so as to be able to communicate with one another.

The input circuitry 101 includes a mouse, a keyboard, a button, a panel switch, a touch command screen, a foot switch, a trackball, a joystick, and/or the like and is configured to receive various types of instructions and setting requests from the operator of the image processing apparatus 100. The input circuitry 101 is configured to output the various types of instructions and setting requests received, to the processing circuitry 120.

The display 102 is configured to display medical image data taken by a medical image diagnosis apparatus and to display a Graphical User Interface (GUI) used by the user to input the various types of setting requests via the input circuitry 101. The medical image diagnosis apparatus is, for example, an apparatus configured to take one or more images of a patient and to generate the medical image data. The medical image diagnosis apparatus may be, for example, an X-ray Diagnosis apparatus, an X-ray Computed Tomography (CT) apparatus, an MRI apparatus, a SPECT apparatus, a PET apparatus, a SPECT-CT apparatus in which a SPECT apparatus and an X-ray CT apparatus are integrated together, a PET-CT apparatus in which a PET apparatus and an X-ray CT apparatus are integrated together, a PET-MRI apparatus in which a PET apparatus and an MRI apparatus are integrated together, or a group of apparatuses made up of any of these apparatuses.

The storage circuitry 110 is configured to store therein various types of computer programs (hereinafter, "programs") used for displaying the medical image data and the GUI, as well as information used by the programs. For example, the storage circuitry 110 stores therein a group of medical image data 111 and a group of medical case data (hereinafter, "group of case data") 112. The storage circuitry 110 is an example of storage units.

The group of medical image data 111 includes a plurality of pieces of medical image data. For example, the group of medical image data 111 includes a plurality of pieces of medical image data taken by a predetermined medical image diagnosis apparatus on mutually-different examination dates/times. For example, the group of medical image data 111 is stored while being kept in correspondence with a patient ID, an examination ID, an apparatus ID, a series ID, and the like, for each of the medical examinations.

In one example, the group of medical image data 111 includes pieces of MRI image data obtained by imaging the head (the brain) of a patient by using an MRI apparatus. The MRI image data may be, for example, three-dimensional medical image data (volume data) that makes it possible to display an arbitrary Multi Planar Reconstruction (MPR) cross-sectional plane.

The group of medical image data 111 does not necessarily have to be MRI image data, and various types of image data that can be used for analyzing diseases are applicable. To analyze Alzheimer's disease, for example, the group of medical image data 111 may be represented by images taken by using various types of biomarkers used for diagnosing progress of Alzheimer's disease. In a specific example, the group of medical image data 111 may be represented by images taken by a PET apparatus by using Pittsburgh Compound B (PiB) serving as a labeled compound (a tracer) for Amyloid beta protein (Aβ), T807, THK-5117, or PBB3 serving as a labeled compound for tau protein, Fluorodeoxyglucose (FDG) used for observing carbohydrate metabolism of the brain, or the like. Further, the group of medical image data 111 may be represented by image data taken by performing a functional Magnetic Resonance Imaging (fMRI) process that makes it possible to observe hypofunctions of the brain. Further, the group of medical image data 111 may be represented by image data taken by performing SPECT, a Contrast Enhanced (CE) MRI, MRI using an Arterial Spin Labeling (ASL) method, or the like, for the purpose of observing the Cerebral Blood Flow (CBF) or a decrease in the volume of cerebral blood vessels. Further, the group of medical image data 111 may be represented by image data of a Diffusion Tensor Image (DTI) used for observing a decrease in a Fractional Anisotropy (FA) value or an increase in a Mean Diffusivity (MD)/Apparent Diffusion Coefficient (ADC) value. Further, the group of medical image data 111 may be represented by Magnetoencephalography (MEG) that maps magnetic fields generated by electric activities of the brain.

The group of case data 112 includes a plurality of pieces of medical case data (hereinafter, "case data") related to a predetermined disease. In the present example, the case data is data obtained by chronologically recording values of various types of indexes, for each of the patients (the examined subjects) who are affected by the disease serving as an analysis target. For example, each of the pieces of case data is stored while being kept in correspondence with the name of the disease, a patient ID, an examination ID, an apparatus ID, a series ID, and the like.

The processing circuitry 120 is configured to control the overall processes performed by the image processing apparatus 100. For example, as illustrated in FIG. 1, the processing circuitry 120 executes a setting function 121, a generating function 122, an obtaining function 123, an analyzing function 124, and a display controlling function 125. In this situation, for example, the processing functions executed by constituent elements of the processing circuitry 120 illustrated in FIG. 1 such as the setting function 121, the generating function 122, the obtaining function 123, the analyzing function 124, and the display controlling function 125 are recorded in the storage circuitry 110 in the form of computer-executable programs. The processing circuitry 120 is a processor configured to realize the functions corresponding to the programs by reading and executing the programs from the storage circuitry 110. In other words, the processing circuitry 120 that has read the programs has the functions illustrated within the processing circuitry 120 in FIG. 1.

In the first embodiment, an example is explained in which the single processing circuitry (i.e., the processing circuitry 120) realizes the processing functions described below; however, it is also acceptable to structure a processing circuitry by combining together a plurality of independent processors, so that the processors realize the functions by executing the programs.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processor realizes the functions by reading and executing the programs stored in the storage circuit. It is also acceptable to directly incorporate the programs into the circuit of the processor, instead of storing the programs in the storage circuitry 110. In that situation, the processor realizes the functions by reading and executing the programs incorporated in the circuit thereof. Further, as for the processors according to the first embodiment, each of the processors may be structured as a single circuit. Alternatively, it is also acceptable to realize the functions thereof by structuring a single processor by combining together a plurality of independent circuits. Further, it is also acceptable to realize the functions thereof by integrating the plurality of constituent elements illustrated in the drawings into a single processor.

The setting function 121 is configured to set conditions related to the patient. For example, the setting function 121 sets the conditions related to the patient for the purpose of extracting a piece of case data corresponding to the conditions of the patient from the group of case data. In this situation, the conditions related to the patient include various types of information related to the state of the patient such as, for example, a cognitive score, a genotype, a family history, whether the patient has been treated or not, and the state of health. The setting function 121 is an example of setting units.

For example, by using the input circuitry 101, the operator inputs conditions such as a cognitive score, a genotype, a family history, whether the patient has been treated, the state of health, and the like. When the operator has input the conditions, the setting function 121 sets the input conditions as the conditions related to the patient. After that, the setting function 121 outputs the conditions related to the patient that were set, to the generating function 122.

The processes performed by the setting function 121 described above are merely examples. For instance, instead of receiving the input from the operator, the setting function 121 may set the conditions related to the patient by, for example, obtaining information corresponding to the conditions of the patient, from information registered in an electronic medical record system or the like.

The generating function 122 is configured to generate a progress model on the basis of the piece of case data corresponding to the conditions set by the setting function 121 among the plurality of pieces of case data stored in the storage circuitry 110. In this situation, for example, the progress model is information indicating a transition of an index in the piece of case data corresponding to the conditions of the patient, among the group of case data 112. The generating function 122 is an example of generating units.

For example, from the group of case data 112 stored in the storage circuitry 110, the generating function 122 extracts a plurality of pieces of case data corresponding to the conditions set by the setting function 121. For example, the generating function 122 extracts the plurality of pieces of case data corresponding to the conditions such as the cognitive score, the genotype, the family history, whether the patient has been treated, the state of health, and the like. After that, as the progress model, the generating function 122 generates an average transition of values of the index contained in the extracted pieces of case data. More specifically, the generating function 122 generates the progress model for each of a plurality of sites in the brain such as the medial temporal lobe (the entorhinal cortex, the hippocampus, and the amygdala), the nucleus basalis of Meynert, the medial septal nucleus, the lateral temporal cortex, the medial parietal lobe, the lateral parietal lobe, the frontal lobe, and the like.

Figure 2A:
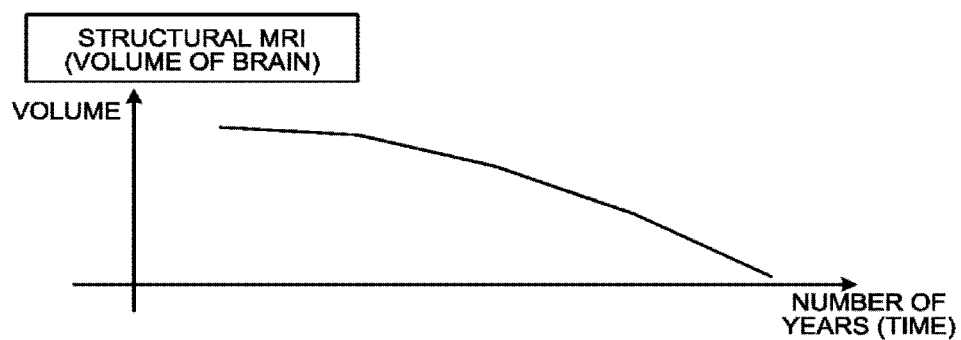
FIGS. 2A and 2B are drawings for explaining processes performed by a generating function according to the first embodiment.
Figure 2B:
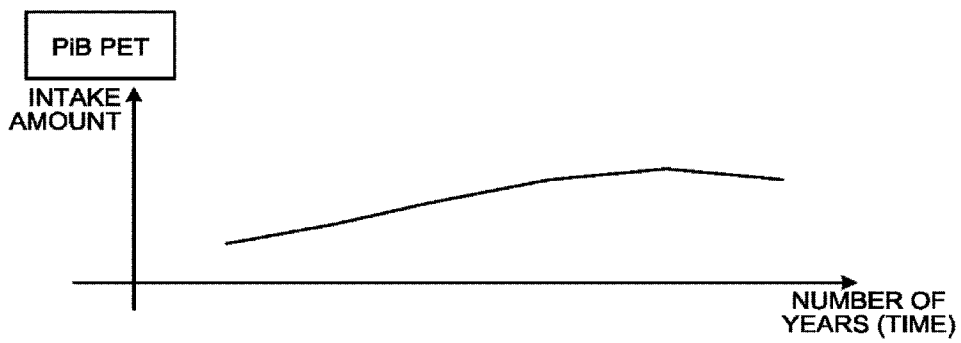

FIGS. 2A and 2B are drawings for explaining processes performed by the generating function 122 according to the first embodiment. FIG. 2A is an example of a progress model ("Structural MRI") indicating a chronological transition of the volume of the hippocampus, which is one of the sites in the brain. In FIG. 2A, the horizontal axis expresses the number of years (time), whereas the vertical axis expresses the volume of the hippocampus. Further, FIG. 2B is an example of a progress model ("PiB PET") indicating a chronological transition of a PiB intake amount of the hippocampus. In FIG. 2B, the horizontal axis expresses the number of years (time), whereas the vertical axis expresses the PiB intake amounts of the hippocampus. To compare values among different patients while using a certain reference level, the values (the index values) on the vertical axis are normalized (subject to normalization). The normalization is performed for the purpose of reducing individual differences where, for example, patients whose volume of the brain are larger to begin with are prone to wrongly exhibit a larger change in the volume (i.e., exhibit a different absolute value). For example, the values on the vertical axis are expressed by using ratios (scores) each taking a value in a healthy state or a value at an onset as 100%.

As illustrated in FIG. 2A, for example, the generating function 122 chronologically plots values indicating the volume of the hippocampus contained in the extracted plurality of pieces of case data, while using the time of the onset as a reference point. In this situation, each of the values indicating the volume of the hippocampus is expressed as a ratio that uses a value in a healthy state as 100%. After that, the generating function 122 generates a progress model by calculating an approximate curve while using the plotted data. In other words, the generating function 122 generates a mathematical function V(t) indicating the volume V corresponding to the number of years t, as the progress model.

Further, as illustrated in FIG. 2B, for example, the generating function 122 chronologically plots the PiB intake amounts contained in the extracted plurality of pieces of case data while using the time of an onset as a reference point. In this situation, each of the PiB intake amounts is expressed as a ratio that uses the value at the time of the onset as 100%. After that, the generating function 122 generates a progress model by calculating an approximate curve while using the plotted data.

As explained above, the generating function 122 generates the progress models on the basis of the pieces of case data corresponding to the conditions of the patient. The processes performed by the generating function 122 described above are merely examples. For instance, the generating function 122 is capable of generating a progress model with respect to an arbitrary site and an arbitrary index, in correspondence with a disease serving as an analysis target. Further, the approximate curves calculated by the generating function 122 may be calculated by using any conventionally-known technique. Further, the progress models do not necessarily have to use approximate curves as long as each of the progress models represents a mathematical function of index values with respect to time.

The obtaining function 123 is configured to obtain values of an index related to a predetermined disease for each of the plurality of sites in the brain, on the basis of a plurality of pieces of medical image data obtained by imaging the brain of the patient at each of a plurality of points in time. The obtaining function 123 obtains the values of a plurality of types of indexes. The obtaining function 123 is an example of obtaining units.

For example, the obtaining function 123 obtains the plurality of pieces of medical image corresponding to the plurality of points in time, from the storage circuitry 110. Further, by performing a segmentation process on the obtained pieces of medical image data, the obtaining function 123 detects each of the plurality of sites in the brain. In one example, the obtaining function 123 automatically detects the sites (through a labeling process) from volume data of the brain of the patient, by using probability information indicating a probability that characteristic points of the plurality of sites may appear, regarding the sites such as the hippocampus, the amygdala, the nucleus basalis of Meynert, and the like. After that, the obtaining function 123 calculates the index values for each of the detected sites.

Figure 3A:
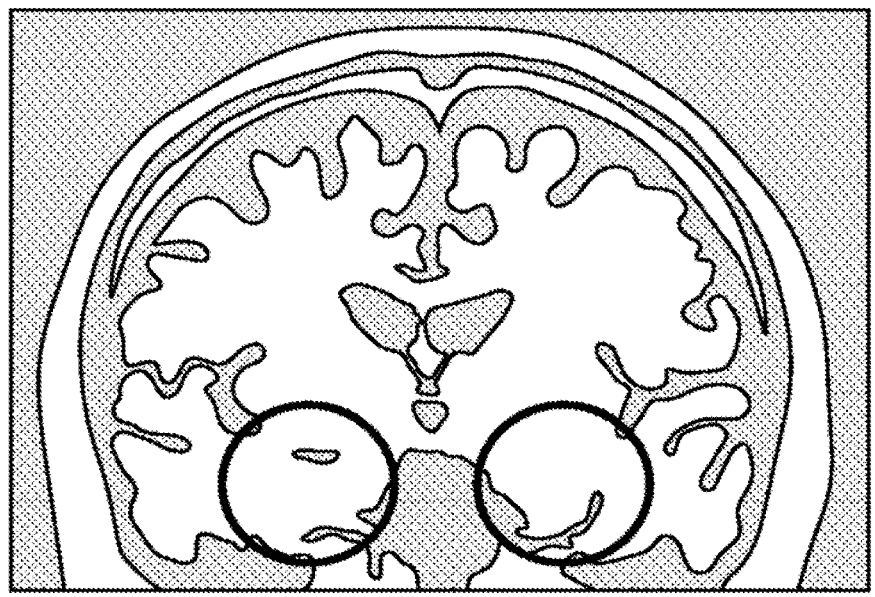
FIGS. 3A and 3B are drawings for explaining processes performed by an obtaining function according to the first embodiment.
Figure 3B:
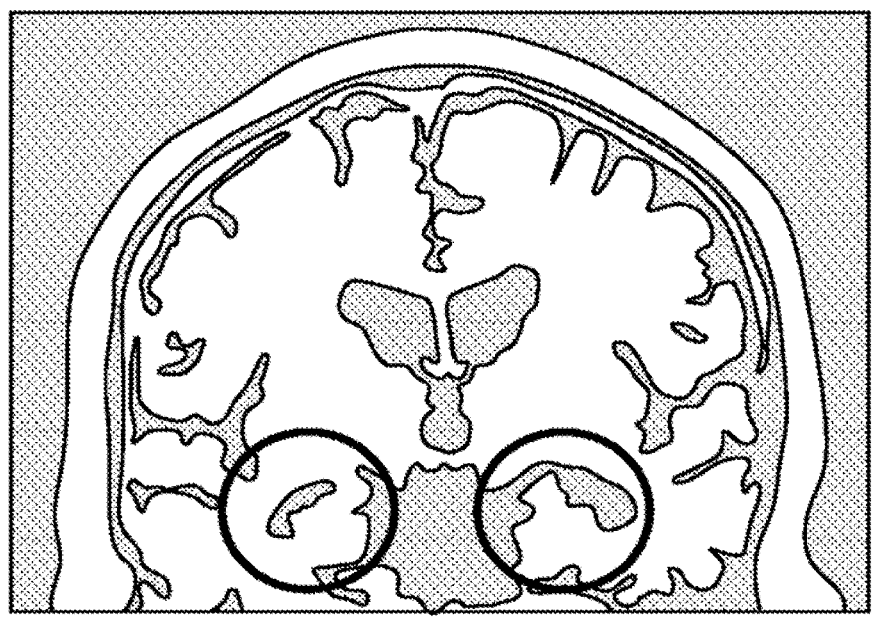
Figure 4A:
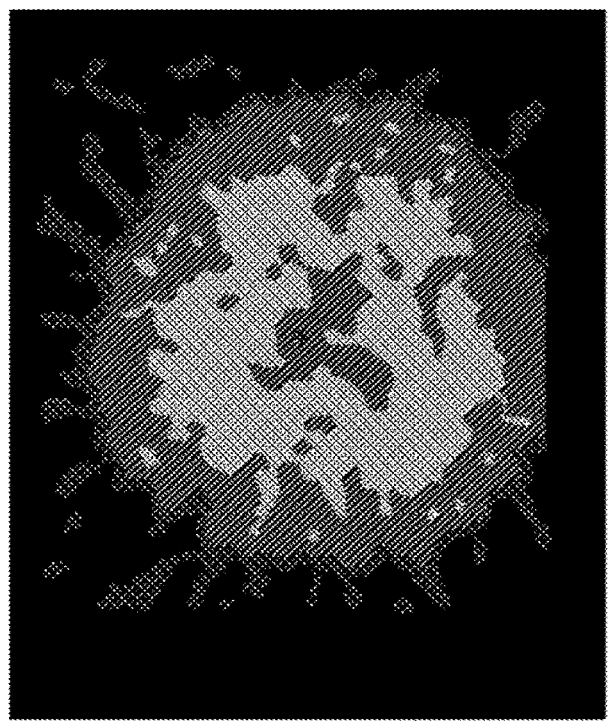
FIGS. 4A and 4B are drawings for explaining processes performed by the obtaining function according to the first embodiment.
Figure 4B:
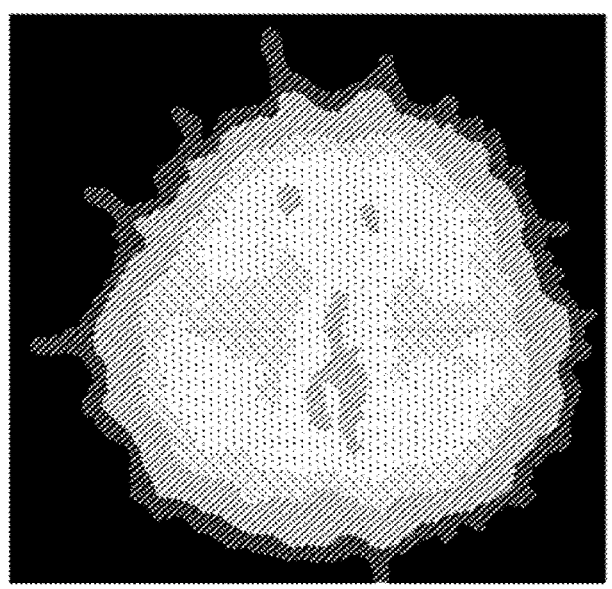

FIGS. 3A, 3B, 4A, and 4B are drawings for explaining processes performed by the obtaining function 123 according to the first embodiment. FIG. 3A illustrates an MRI image of the brain of a healthy person. FIG. 3B illustrates an MRI image of the brain of an examined subject (a patient). FIG. 4A illustrates a PiB-PET image of the brain of a healthy person. FIG. 4B illustrates a PiB-PET image of the brain of an examined subject (a patient).

As illustrated in FIGS. 3A and 3B, the obtaining function 123 detects each of the plurality of sites by performing a segmentation process on the MRI images of the brain. Further, the obtaining function 123 calculates the volume of each of the sites, on the basis of the size of the region of each of the detected sites. For example, the obtaining function 123 calculates the volume of each of the plurality of sites such as the hippocampus, the amygdala, the nucleus basalis of Meynert, and the like. The examples in FIGS. 3A and 3B indicate that the volume of the hippocampus has decreased (atrophy) (see the regions indicated with the circles).

As indicated in FIGS. 4A and 4B, the obtaining function 123 detects each of the plurality of sites, by performing a segmentation process on the PiB-PET images of the brain. In this situation, in the PiB-PET images, a brightness value (a pixel value) corresponding to the PiB intake amount is assigned to each of the pixels. On the basis of the brightness value of each of the pixels included in the regions of the detected sites, the obtaining function 123 calculates a PiB intake amount for each of the sites. For example, the obtaining function 123 calculates the PiB intake amount of each of the plurality of sites such as the hippocampus, the amygdala, the nucleus basalis of Meynert, and the like.

As explained above, the obtaining function 123 obtains the index values corresponding to the disease such as the volume values and the PiB intake amounts, for each of the sites. The processes performed by the obtaining function 123 described above are merely examples. For instance, the obtaining function 123 is capable of calculating an arbitrary index value for each arbitrary site, in correspondence with a disease serving as an analysis target. Further, when some already-calculated index values are present, the obtaining function 123 may directly obtain the index values. For example, when some index values have already been calculated from results of medical examinations performed in the past, the obtaining function 123 may obtain the index values from the examination results and omit the process of calculating index values from the image data. Further, the process performed by the obtaining function 123 to detect the plurality of sites is not limited to the segmentation process. For example, the obtaining function 123 may perform the detecting process by performing a position aligning process (a matching process) with a segmented standard brain. In that situation, the obtaining function 123 performs the position aligning process between image data of the standard brain in which the sites are labeled in advance, with image data of the brain of the patient. After that, the obtaining function 123 performs a segmentation process on the brain of the patient, by changing the shape of each of the sites in the standard brain so as to fit the shape of the brain of the patient.

The analyzing function 124 is configured to analyze, for each of the plurality of sites, a relationship between changes in the value at the plurality of points in time and the progress model indicating changes in the index through progress of a predetermined disease. For example, by fitting the progress model to the changes in the index value, the analyzing function 124 generates a shape-modified progress model obtained by changing the shape of the progress model. For example, the analyzing function 124 analyzes the relationship between the changes in the value at the plurality of points in time and the progress model indicating the changes in the index through the progress of the predetermined disease, by using the progress model generated by the generating function 122. The analyzing function 124 is an example of analyzing units.

Figure 5A:
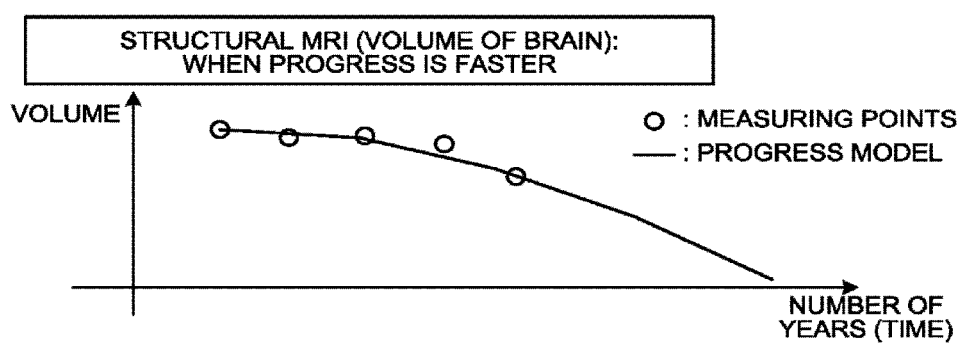
FIGS. 5A and 5B are drawings for explaining processes performed by an analyzing function according to the first embodiment.
Figure 5B:
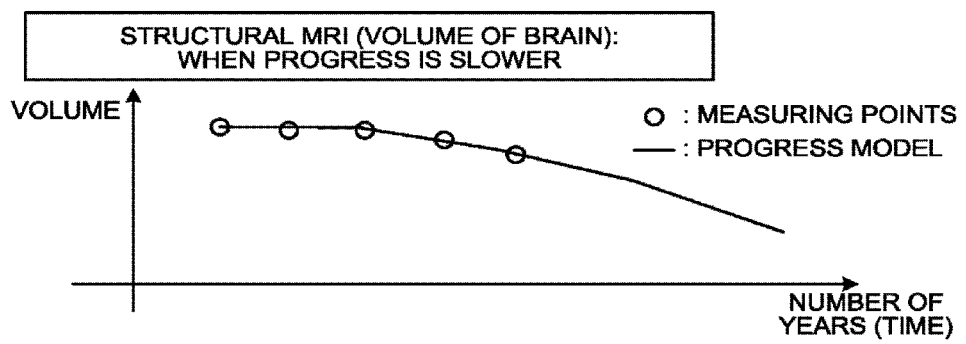
Figure 6A:
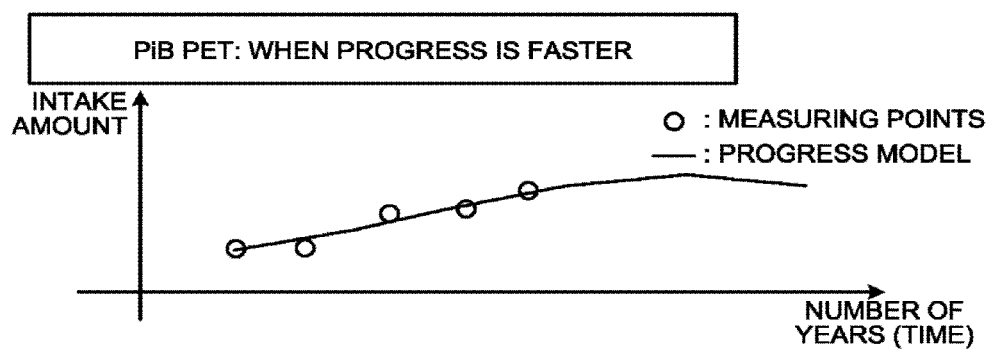
FIGS. 6A and 6B are drawings for explaining processes performed by the analyzing function according to the first embodiment.
Figure 6B:
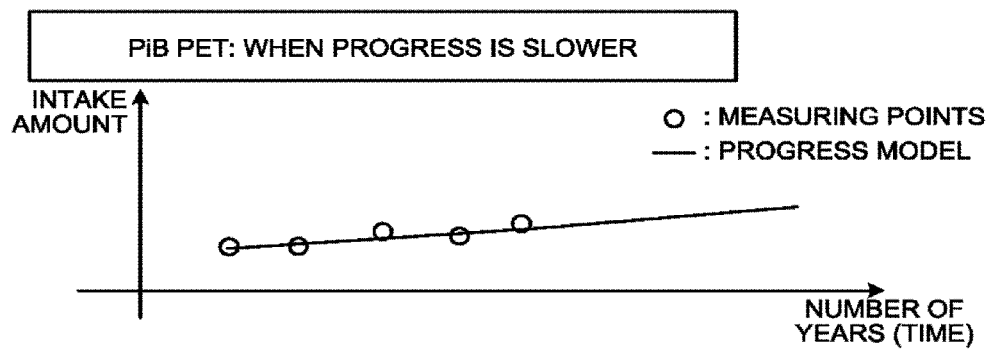

FIGS. 5A, 5B, 6A, and 6B are drawings for explaining processes performed by the analyzing function 124 according to the first embodiment. FIG. 5A illustrates an example of a process performed when the progress of the disease is faster, while the structural MRI is used. FIG. 5B illustrates an example of a process performed when the progress of the disease is slower, while the structural MRI is used. FIG. 6A illustrates an example of a process performed when the progress of the disease is faster, while PiB-PET is used. FIG. 6B illustrates an example of a process performed when the progress of the disease is slower, while PiB-PET is used. In FIGS. 5A and 5B, the horizontal axis expresses the number of years (time), whereas the vertical axis expresses the volume of the hippocampus. Further, in FIGS. 6A and 6B, the horizontal axis expresses the number of years (time), whereas the vertical axis expresses PiB intake amounts of the hippocampus. Further, the small circles indicate the values (the measuring points) of the index values calculated from the image data of the patient. The rigid lines indicate the progress models.

As illustrated in FIGS. 5A and 5B, for example, the analyzing function 124 determines the volume of the hippocampus of the patient at the earliest point in time among the volume values of the hippocampus of the patient corresponding to the plurality of points in time to be the value in a healthy state and further arranges the volume in the healthy state in the progress model to be equal to the determined value. After that, the analyzing function 124 changes the shape of the progress model in the time direction in such a manner that the volume values in the other points in time become equal to (approximate to) the progress model. For example, when the disease of the patient progresses faster than the progress model, the analyzing function 124 generates a shape-modified progress model obtained by reducing the progress model, by reducing the progress model in the time direction, as illustrated in FIG. 5A. On the contrary, for example, when the disease of the patient progresses more slowly than the progress model, the analyzing function 124 generates a shape-modified progress model obtained by enlarging the progress model, by enlarging the progress model in the time direction, as illustrated in FIG. 5B. In this manner, the analyzing function 124 fits the progress model to the volume values of the hippocampus of the patient.

Further, as illustrated in FIGS. 6A and 6B, for example, the analyzing function 124 determines the PiB intake amount of the hippocampus of the patient at the earliest point in time among the intake amounts of the patient corresponding to the plurality of points in time to be the value in a healthy state and further arranges the intake amount in the healthy state in the progress model to be equal to the determined value. After that, the analyzing function 124 changes the shape of the progress model in the time direction in such a manner that the intake amounts at the other points in time become equal to (approximate to) the progress model. For example, when the disease of the patient progresses faster than the progress model, the analyzing function 124 generates a shape-modified progress model obtained by reducing the progress model, by reducing the progress model in the time direction, as illustrated in FIG. 6A. On the contrary, for example, when the disease of the patient progresses more slowly than the progress model, the analyzing function 124 generates a shape-modified progress model obtained by enlarging the progress model, by enlarging the progress model in the time direction, as illustrated in FIG. 6B. In this manner, the analyzing function 124 fits the progress model to the PiB intake amount of the hippocampus of the patient.

As explained above, the analyzing function 124 analyzes, for each of the plurality of sites, the relationship between the chronological changes in each of the plurality of types of index values and the progress model. The processes performed by the analyzing function 124 described above are merely examples. For example, the analyzing function 124 is capable of analyzing a relationship between changes in the index value of an arbitrary site and an arbitrary progress model, in correspondence with any disease serving as an analysis target.

Further, in the description above, the example is explained in which, while using the value at the earliest point in time as the value in the healthy state, the index value in the healthy state in the progress model is arranged to be equal thereto; however, possible embodiments are not limited to this example. For instance, the obtaining function 123 may perform the analysis by using a number of years and an index value designated by the operator as the index value of the patient in the healthy state. Alternatively, for example, the obtaining function 123 may calculate an approximate curve of a plurality of measuring points and may change the shape of the progress model in such a manner that the approximate curves and the progress model become equal to each other.

The display controlling function 125 is configured to cause the display 102 to display the analysis result for each of the plurality of sites resulting from the analysis by the analyzing function 124. For example, the display controlling function 125 causes the display 102 to display in such a manner that a comparison can be made between the changes in the index value and the progress model. Next, first to third display examples resulting from processes performed by the display controlling function 125 will be explained.

First Display Example

FIG. 7 is a drawing for explaining the first display example resulting from a process performed by the display controlling function 125 according to the first embodiment. For example, the top section of FIG. 7 illustrates an example of an analysis result regarding PiB intake amounts of a plurality of sites. In the top section of FIG. 7, the horizontal axis expresses the number of years (time), whereas the vertical axis expresses PiB intake amounts of the hippocampus. Further, the small circles indicate the intake amounts (the measuring points) calculated from the image data of the patient. The rigid lines indicate shape-modified progress models fitted to the index values of the patient by the analyzing function 124. The indication MTC denotes the medial temporal cortex; the indication LTC denotes the lateral temporal cortex; the indication MPC denotes the medial parietal cortex; the indication LPC denotes the lateral parietal cortex; and the indication FC denotes the frontal cortex. Further, the bottom section of FIG. 7 illustrates a radar chart regarding current intake amounts of the various sites.

As illustrated in the top section of FIG. 7, for example, the display controlling function 125 displays the PiB intake amount (the small circle) at each of the plurality of sites and a shape-modified progress model (the rigid line) in such a manner that a comparison can be made therebetween. Further, as illustrated in the bottom section of FIG. 7, the display controlling function 125 displays the intake amount values at the current point in time in the radar chart.

As explained above, the display controlling function 125 displays the index values at each of the plurality of sites and the shape-modified progress model in such a manner that a comparison can be made therebetween. In other words, by displaying the measuring points and the progress model at the same time, the display controlling function 125 is able to make clear the difference between the measuring points and the progress model. The process performed by the display controlling function 125 described above is merely an example. For example, although FIG. 7 illustrates the example in which the changes in the certain index value at the plurality of sites are displayed in such a manner that a comparison can be made with the progress models, possible embodiments are not limited to this example. For instance, when index values of a plurality of types are calculated, the display controlling function 125 may display changes in the index values of the plurality of types in such a manner that a comparison can be made with progress models. For example, with regard to the volume values and the PiB intake amounts of the hippocampus, the display controlling function 125 may display chronological changes in the index values and the progress models in such a manner that a comparison can be made therebetween. Further, for example, the display controlling function 125 does not necessarily have to display both of the charts in the top and the bottom sections of FIG. 7 at the same time. For instance, the display controlling function 125 may display one of the charts illustrated in the top and the bottom sections of FIG. 7 and may switch between the displays of the two charts in response to an instruction from the operator.

Second Display Example

Figure 8:
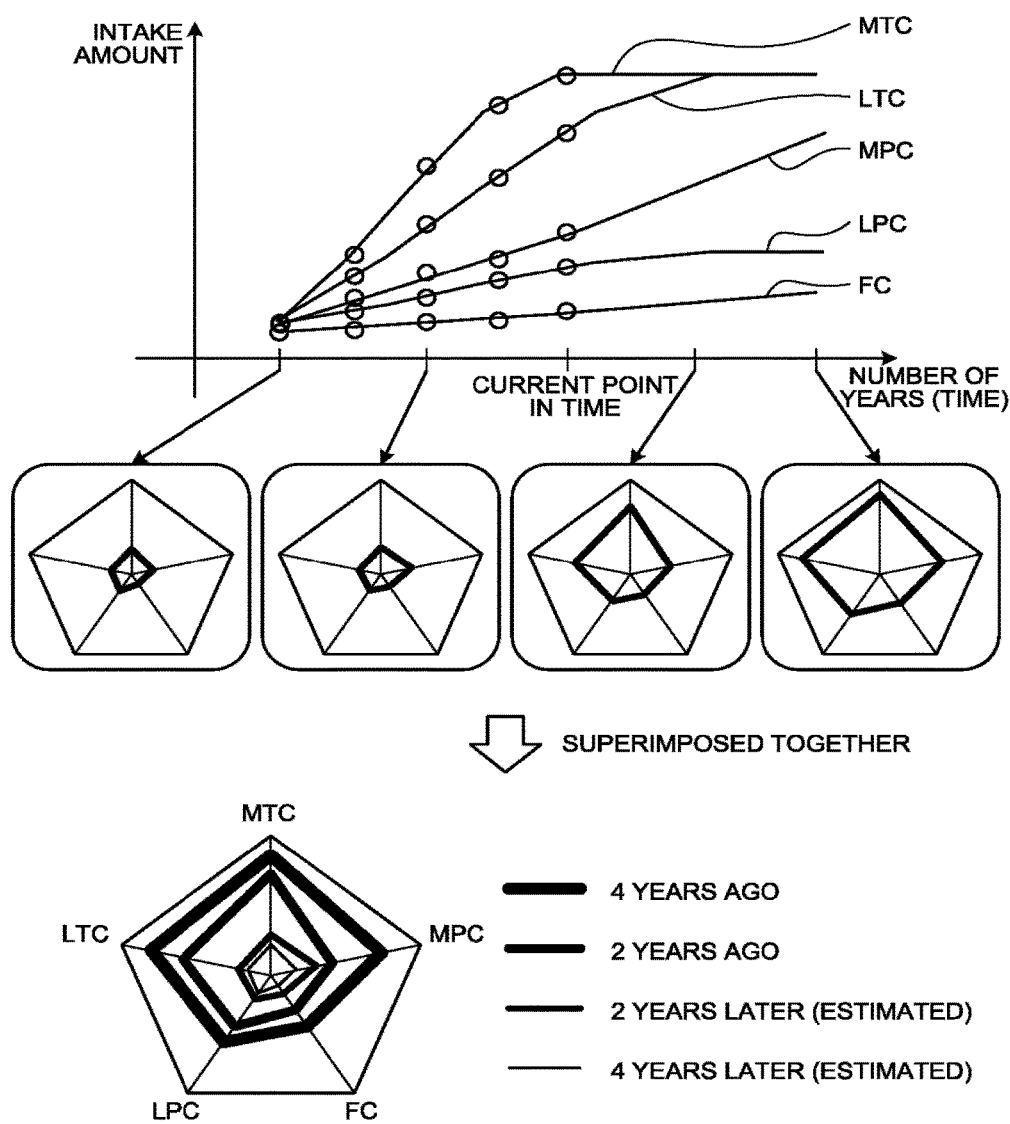
FIG. 8 is a drawing for explaining a second display example resulting from a process performed by the display controlling function according to the first embodiment.

FIG. 8 is a drawing for explaining a second display example resulting from a process performed by the display controlling function 125 according to the first embodiment. For example, the top section of FIG. 8 illustrates a chart same as the chart in the top section of FIG. 7. Further, the middle section of FIG. 8 illustrates radar charts regarding the intake amounts at the various sites corresponding to the points in time (the numbers of years) in the top section of FIG. 8. Further, the bottom section of FIG. 8 illustrates a chart obtained by superimposing together the radar charts in the middle section of FIG. 8.

As illustrated in the middle and the bottom sections of FIG. 8, the display controlling function 125 displays the intake amount values at the different points in time in the radar charts. In this situation, as for the values in the radar charts corresponding to two years later and four years later, the display controlling function 125 displays the values (estimated values/future prediction values) in the shape-modified progress model (in the top section of FIG. 8). In contrast, in the radar charts corresponding to the times earlier than the current point in time, the display controlling function 125 displays the measured values of the patient.

As explained above, in the radar charts, the display controlling function 125 displays the index values and the future estimated values at the plurality of points in time. The process performed by the display controlling function 125 described above is merely an example. For instance, although the bottom section of FIG. 8 illustrates the example in which the measured values of the patient are displayed in the radar charts corresponding to the times earlier than the current point in time, possible embodiments are not limited to this example. For instance, also in the radar charts corresponding to the times earlier than the current point in time, the display controlling function 125 may display the values in the shape-modified progress models. With this arrangement, when the measured values include one or more errors, for example, it is possible to reduce (absorb) the errors by displaying the values in the shape-modified progress models.

Third Display Example

Figure 9:
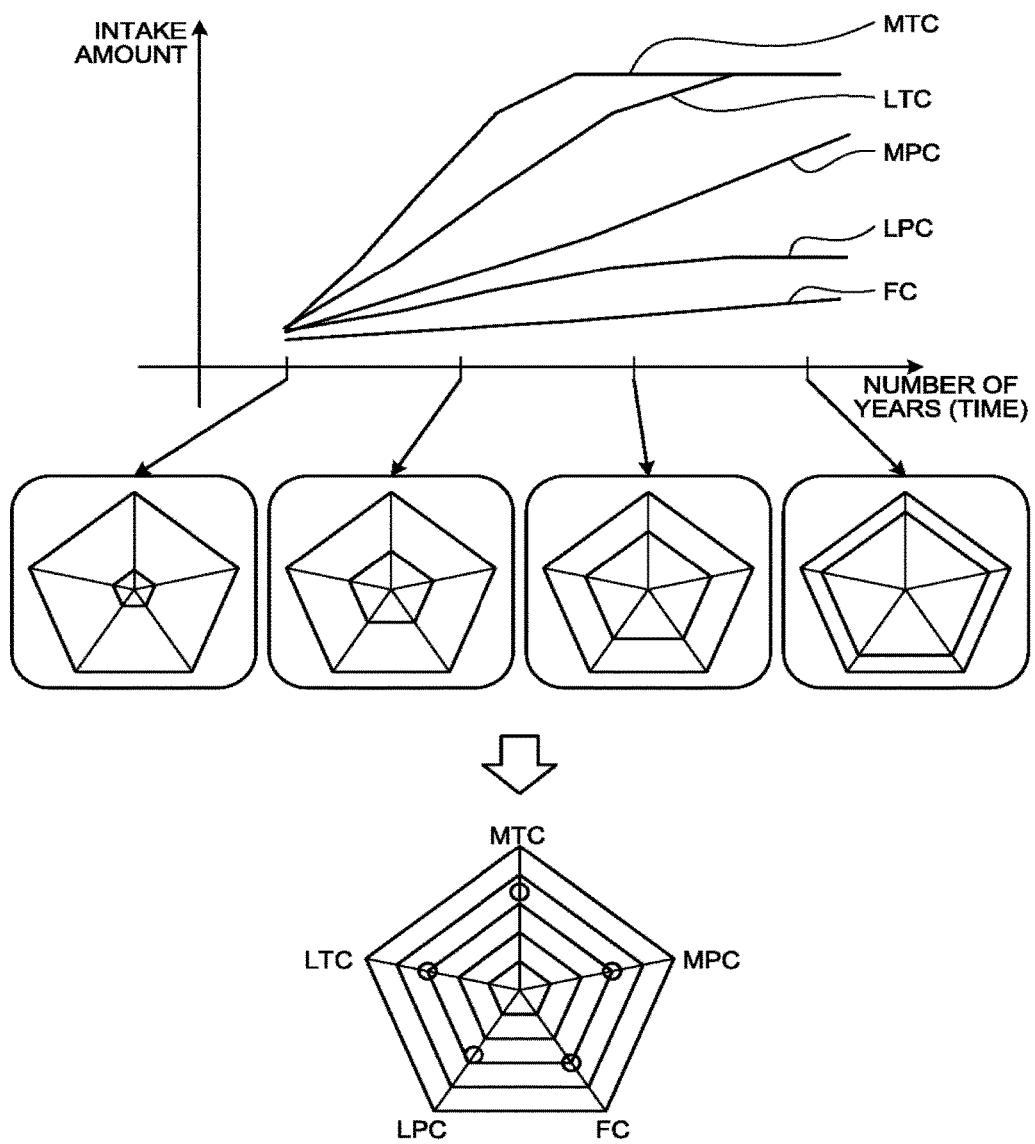
FIG. 9 is a drawing for explaining a third display example resulting from a process performed by the display controlling function according to the first embodiment.

FIG. 9 is a drawing for explaining a third display example resulting from a process performed by the display controlling function 125 according to the first embodiment. For instance, the top section of FIG. 9 illustrates a chart similar to the chart in the top section of FIG. 7, except that the measuring points of the patient are not displayed. Further, the middle section of FIG. 9 illustrates an example of a process of adjusting the scales on the axes of the radar charts so that a regular pentagon is formed by the straight lines connecting together the values in the shape-modified progress models of the various sites corresponding to each of the different points in time (the numbers of years). Further, the bottom section of FIG. 9 illustrates an example in which the index values of the patient are displayed in a radar chart of which the scales on the axes have been adjusted so that a regular pentagon is formed by the straight lines connecting together the values in the shape-modified progress models at each of the different points in time.

As illustrated in the middle section of FIG. 9, the display controlling function 125 adjusts the scales on the axes of the radar charts in such a manner that a regular pentagon is formed by the lines connecting together the intake amounts at the various sites corresponding to mutually-the-same point in time in the progress models. More specifically, the display controlling function 125 adjusts the scales on the axes of the radar charts in such a manner that a regular pentagon is formed by the intake amounts in the shape-modified progress models at each of the different points in time. In this situation, the display controlling function 125 makes the adjustments so that the sizes of the regular pentagons corresponding to the different points in time become larger in correspondence with the passing of the time. For example, as illustrated by the first chart from the left-hand side in the middle section of FIG. 9, the display controlling function 125 adjusts the scale on the axes of the radar chart corresponding to the various sites, in such a manner that a small pentagon is formed by the lines connecting together the intake amounts of the various sites in the healthy state. Further, for example, as illustrated by the second chart from the left-hand side in the middle section of FIG. 9, the display controlling function 125 adjusts the scale on the axes of the radar chart corresponding to the various sites, in such a manner that a pentagon larger than the pentagon in the healthy state is formed by the lines connecting together the intake amounts of the various sites observed when a predetermined period of time has elapsed since the time in the healthy state. As explained herein, the display controlling function 125 adjusts the scales on the axes of the radar charts corresponding to the various sites, in such a manner that the sizes of the regular pentagons become larger in correspondence with the passing of the time.

Further, as illustrated in the bottom section of FIG. 9, the display controlling function 125 displays the measured values of the patient (the small circles in the drawing) in the radar chart adjusted in such a manner that the intake amounts in the shape-modified progress models form the regular pentagons. With these arrangements, for example, the operator is able to easily understand whether the changes in the index at each of the plurality of sites are in line with the progress models by comparing the regular pentagons with the measured values. Further, for example, when the measured values of the patient form an irregular pentagon, because the operator is led to suspect that the patient may have another disease besides the targeted disease, it is possible to detect the other disease at an early stage.

As explained above, the display controlling function 125 displays the values in the radar chart in which the regular polygon is formed by the lines connecting the values of the index (which may simply be referred to as "index values") at the various sites in the progress models corresponding to mutually-the-same point in time. The process performed by the display controlling function 125 described above is merely an example. For instance, with reference to FIG. 9, the example is explained in which the scales on the axes of the radar charts are adjusted in such a manner that the index values of the progress models form the regular pentagons; however, possible embodiments are not limited to this example. For instance, the scales on the axes of the radar charts may be adjusted in such a manner that the index values of the progress models form any regular polygons (e.g., regular quadrangles or regular hexagons) corresponding to the number of axes.

As explained above, the display controlling function 125 displays the analysis result in an arbitrary display mode selected from among the first to the third display examples. Further, the display controlling function 125 may display the analysis result by combining any of the display modes in the first to the third display examples as appropriate. For instance, the display controlling function 125 is also capable of switching between the display modes in the first to the third display examples as appropriate, in response to an instruction from the operator.

Further, for example, although the bottom section of FIG. 9 illustrates the example in which the changes in the index in the progress models of the disease are displayed by using the regular polygons, possible embodiments are not limited to this example. For instance, if there are normal models each indicating normal changes in the index due to aging, the display controlling function 125 may realize a display in such a manner that the changes in the index in the normal models form a regular polygon. In other words, the display controlling function 125 displays the values in the radar chart in which a regular polygon is formed by the lines connecting together the values of the index at the various sites corresponding to mutually-the-same point in time in the normal models indicating the normal changes in the index due to aging.

In the explanation above, the example is explained in which the display controlling function 125 displays the analysis result in the chart; however, possible embodiments are not limited to this example. For instance, the display controlling function 125 may display a table or numerical value data serving as a base of the chart. The display controlling function 125 may output a table in which the intake amounts are kept in correspondence with the numbers of years (the time) or may output a table in a Comma Separated Value (CSV) file.

Further, for example, the output destination to which the display controlling function 125 outputs the analysis result is not limited to the display 102. For example, the display controlling function 125 may transmit the analysis result to an arbitrary apparatus connected via a network. More specifically, the display controlling function 125 may transmit the analysis result to a server configured to manage data in a hospital in a concentrated manner or an apparatus (e.g., a report generating apparatus) configured to generate a diagnosis report. Further, for example, the display controlling function 125 may store the analysis result into a recording medium such as a Digital Versatile Disc (DVD). In other words, the display controlling function 125 is capable of executing the processes as an output controlling function configured to arrange the analysis result resulting from the analysis performed by the analyzing function 124 and corresponding to each of the plurality of sites, to be output.

Figure 10:
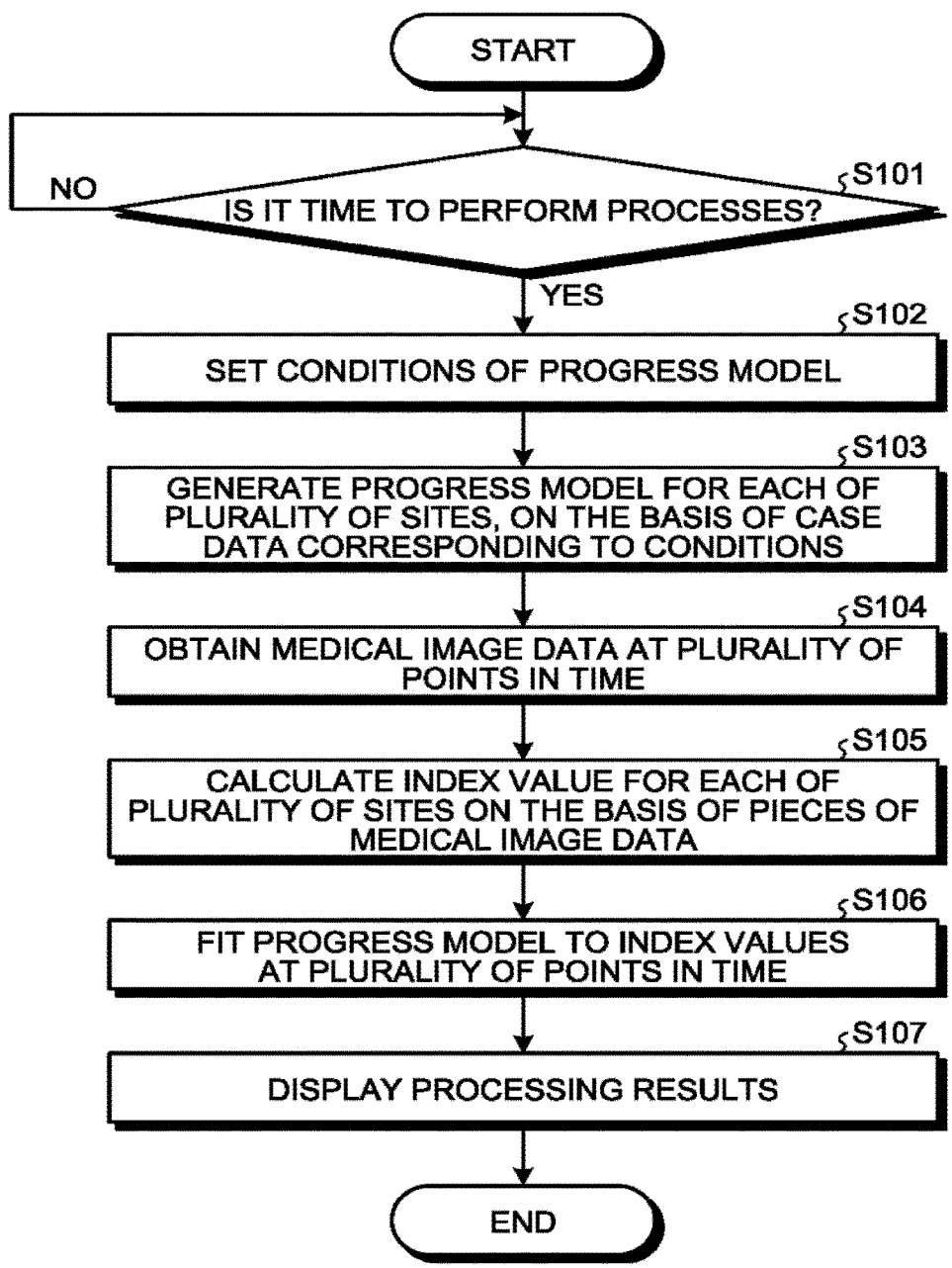
FIG. 10 is a flowchart illustrating a processing procedure performed by the image processing apparatus according to the first embodiment.

FIG. 10 is a flowchart illustrating a processing procedure performed by the image processing apparatus 100 according to the first embodiment. The processing procedure in FIG. 10 is started, for example, when an instruction is received from the operator indicating that an analysis related to progress of a disease should be started.

At step S101, the processing circuitry 120 judges whether it is time to perform the processes. For example, when an instruction is received from the operator indicating that an analysis related to progress of a disease should be started, the processing circuitry 120 determines that it is time to perform the processes and proceeds to the processes at step S102 and thereafter. On the contrary, when the judgment result at step S101 is in the negative, the processes at step S102 and thereafter are not performed, and the processing functions such as the setting function 121 to the display controlling function 125 are in a standby state.

When the judgment result at step S101 is in the positive, the setting function 121 sets conditions of a progress model at step S102. For example, to extract pieces case data corresponding to conditions of the patient from a group of case data, the setting function 121 sets the conditions related to the patient.

At step S103, the generating function 122 generates a progress model for each of a plurality of sites, on the basis of the pieces of case data corresponding to the conditions. For example, from the group of case data 112 stored in the storage circuitry 110, the generating function 122 extracts the plurality of pieces of case data corresponding to the conditions set by the setting function 121. Further, the generating function 122 generates an average transition of values of the index included in the extracted plurality of pieces case data, as a progress model.

At step S104, the obtaining function 123 obtains medical image data corresponding to a plurality of points in time. For example, the obtaining function 123 obtains a plurality of pieces of medical image data corresponding to the plurality of points in time, from the storage circuitry 110.

At step S105, the obtaining function 123 calculates index values for each of the plurality of sites, on the basis of the pieces of medical image data. For example, by performing a segmentation process on the pieces of medical image data obtained from the storage circuitry 110, the obtaining function 123 detects each of the plurality of sites included in the brain. Further, the obtaining function 123 calculates the index values for each of the detected sites.

At step S106, the analyzing function 124 fits the progress models to the index values corresponding to the plurality of points in time. For example, by fitting each of the progress models to the changes in the index value, the analyzing function 124 generates a shape-modified progress model obtained by changing the shape of the progress model.

At step S107, the display controlling function 125 displays processing results. For example, the display controlling function 125 displays the changes in the index value and the progress models in such a manner that a comparison can be made therebetween. More specifically, the display controlling function 125 displays the analysis result by using an arbitrary display mode selected from among the first to the third display examples.

The processing procedure illustrated in FIG. 10 is merely an example. For example, the processes at steps S102 and S103 in FIG. 10 do not necessarily have to be performed. For example, when a typical transition of an index is known with regard to the disease serving as an analysis target, i.e., when a mathematical function expressing the index corresponding to the numbers of years is known, it is possible to use the mathematical function as a progress model. Accordingly, it is not necessary to perform the processes at steps S102 and S103 that are the processes to generate a progress model. Further, in that situation, the storage circuitry 110 does not necessarily need to have the group of case data 112 stored therein.

As explained above, in the image processing apparatus 100 according to the first embodiment, the obtaining function 123 is configured to obtain the values of the index related to the predetermined disease for each of the plurality of sites included in the brain, on the basis of the plurality of pieces of medical image data obtained by imaging the brain of the patient at each of the plurality of points in time. Further, the analyzing function 124 is configured to analyze, for each of the plurality of sites, the relationships between the changes in the value at the plurality of points in time and the progress models each indicating the changes in the index through the progress of the predetermined disease. The display controlling function 125 is configured to arrange the analysis result for each of the plurality of sites resulting from the analysis performed by the analyzing function 124 to be displayed. With these arrangements, the image processing apparatus 100 makes it possible to easily perform the analysis related to the progress of the disease.

Figure 11:
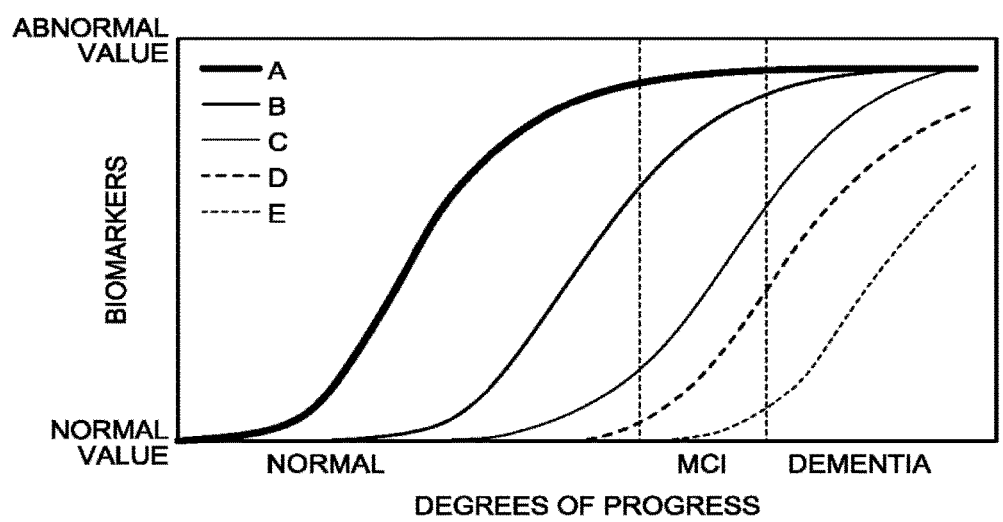
FIG. 11 is a chart for explaining advantageous effects of the image processing apparatus according to the first embodiment.
Figure 12A:
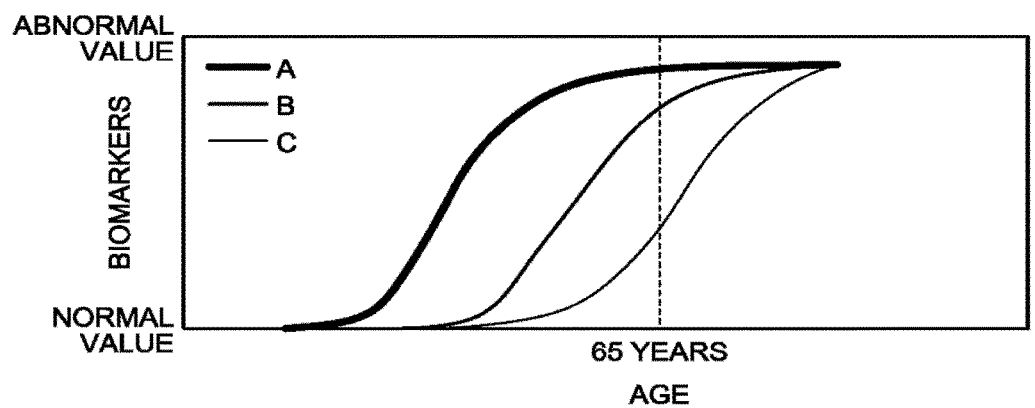
FIGS. 12A and 12B are charts for explaining advantageous effects of the image processing apparatus according to the first embodiment.
Figure 12B:
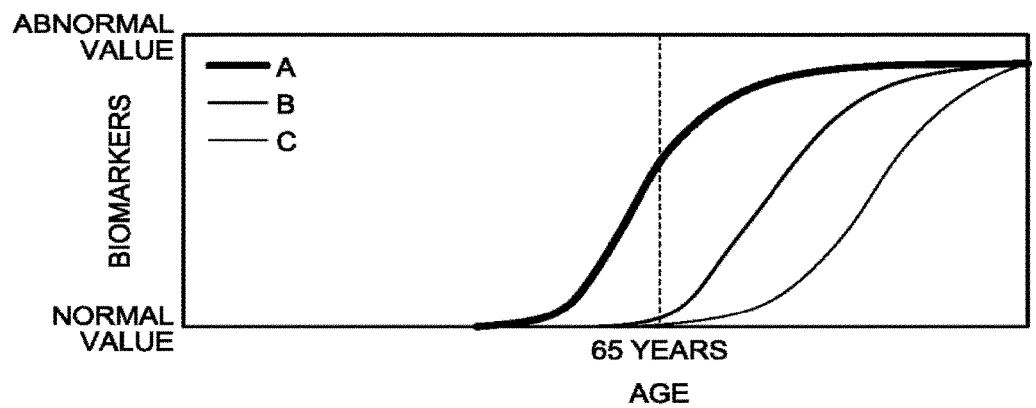

FIGS. 11, 12A, and 12B are drawings for explaining advantageous effects of the image processing apparatus 100 according to the first embodiment. FIG. 11 illustrates an imbalance among the changes in biomarkers observed through progress of Alzheimer's disease. In FIG. 11, the horizontal axis expresses the degree of progress of the disease, whereas the vertical axis expresses changes in the biomarkers (the indexes). FIGS. 12A and 12B illustrate an imbalance among changes in biomarkers corresponding to differences in patient's conditions. In FIGS. 12A and 12B, the horizontal axis express the age of the patient, whereas the vertical axis expresses changes in the biomarkers (the indexes). In FIGS. 11, 12A, and 12B, the characters A to E denote the mutually-different biomarkers. Further, the indication MCI denotes a Mild Cognitive Impairment, which is dementia of a small degree.

As illustrated in FIG. 11, with Alzheimer's disease, through the progress of the disease, the biomarkers that reflect the progress change sequentially. For example, the biomarker A exhibits a rise before the onset of dementia, whereas the biomarker E, in some situations, starts rising even with the MCI. As explained herein, with Alzheimer's disease, the biomarkers that exhibit changes vary depending on the progress of the disease. Further, with Alzheimer's disease, the sites that exhibit atrophy also vary depending on the progress of the disease. For example, at an early stage, atrophy is exhibited in the medial lateral lobe (the entorhinal cortex, the hippocampus, and the amygdala). In the course of the progress of the disease, atrophy sites sequentially change to the nucleus basalis of Meynert, the medial septal nucleus, the lateral temporal cortex, the medial parietal lobe, the lateral parietal lobe, and the frontal lobe. Further, there are other sites such as the striate cortex and the somatosensory area and that are not so easily atrophied even in the course of the progress of the disease. As explained above, with Alzheimer's disease, through the progress of the disease, the indexes and the sites that reflect the progress of disease sequentially change.

In the present example, the image processing apparatus 100 according to the first embodiment is configured to obtain the index values in the time series with respect to the plurality of sites and to display the relationships between the changes in the obtained index values and the progress models. Accordingly, because the image processing apparatus 100 evaluates not only the index value at a single point in time, but also the chronological changes in the index value, i.e., the speed of the change, the image processing apparatus 100 makes it possible to easily perform the analysis related to the progress of the disease. For example, by referring to the analysis results and studying which index from which site changes the most, the operator is able to easily assess the degree of progress of the disease.

Further, as illustrated in FIGS. 12A and 12B, with Alzheimer's disease, changes in the biomarkers exhibit an imbalance depending on the conditions (the state) of the patient. For example, depending on differences in the genotype of Apolipoprotein E (ApoE), the biomarkers may exhibit a rise earlier (FIG. 12A) or later (FIG. 12B).

In this regard, in the image processing apparatus 100 according to the first embodiment, the storage circuitry 110 is configured to store therein a plurality of pieces of case data related to Alzheimer's disease. Further, the setting function 121 is configured to set the conditions related to the patient. Further, among the plurality of pieces of case data stored in the storage circuitry 110, the generating function 122 is configured to generate a progress model on the basis of pieces of case data corresponding to the conditions set by the setting function 121. The analyzing function 124 is configured to analyze the relationship by using the progress model generated by the generating function 122. Consequently, because the image processing apparatus 100 is configured to generate the progress model appropriate for each patient, it is possible to accurately assess the progress of the disease.

Other Embodiments

The present disclosure may be carried out in other various embodiments besides those described above.

For example, in the embodiment above, the example is explained in which the relationships of the plurality of index values with the progress models are displayed; however, possible embodiments are not limited to this example. For instance, the image processing apparatus 100 may analyze and display a relationship between changes in a time series of a single index value at a plurality of sites and progress models.

Displaying a Site Having a High Changing Speed in a Highlighted Manner

Further, for example, the display controlling function 125 may obtain changes in an index for each of a plurality of sites, compare the changing speeds of the obtained changes with one another, and display a site having a higher changing speed than the other sites in a highlighted manner.

For example, at mutually-the-same point in time, the display controlling function 125 calculates the speed (a slope) of a change in the index for each of the plurality of sites. Further, the display controlling function 125 identifies an index having the highest speed (the largest slope) from among the calculated speeds corresponding to the various sites. After that, the display controlling function 125 displays the site corresponding to the identified index in a highlighted manner. In an example, in the chart in the top section of FIG. 7, because LTC has a larger slope at the current point in time, the display controlling function 125 displays the line representing LTC in red (a color different from the colors used for the other sites). With this arrangement, for example, the operator is able to easily recognize the site in which the lesion is progressing fast.

Methods for displaying the site in a highlighted manner are not limited to using a different color. For example, the display controlling function 125 may display the site in which the lesion is progressing fast in a highlighted manner by using a different type of line or may display a message such as "SITE IN WHICH LESION IS PROGRESSING FAST" in correspondence with the site. In other words, the display controlling function 125 may display the identified site in a display mode different from the mode used for displaying the other sites.

Displaying Degrees of Deviation from a Progress Model

Further, for example, the display controlling function 125 may obtain degrees of deviation each indicating a degree by which the value of an index deviates from a progress model and further display the obtained degrees of deviation.

For example, as degrees of deviation, the display controlling function 125 calculates the differences between values of an index at various sites and values in progress models. Further, the display controlling function 125 displays the calculated degrees of deviation. In an example, in the chart in the top section of FIG. 7, the display controlling function 125 displays line segments vertically connecting the rigid lines (the shape-modified progress models) and the small circles (the measuring points). In that situation, the distances (the lengths) of the line segments correspond to the degrees of deviation.

Accordingly, for example, the operator is able to easily conjecture validity as to how much the index values match the standard model of the disease. For example, as compared with a progress model of Alzheimer's disease, when the degrees of deviation of index values at various sites of the patient are smaller or when the degrees of deviation indicate that the values deviate entirely, the operator is able to conjecture that diagnosing the patient with Alzheimer's disease is valid. On the contrary, when the degree of deviation is larger at a specific site of the patient, the operator is able to conjecture that there is a possibility that the patient may not be affected by Alzheimer's disease or there is a possibility that the patient may be affected by another disease together with Alzheimer's disease.

Methods for displaying the degrees of deviation are not limited to the example described above. For instance, the display controlling function 125 may display numerical values corresponding to the degree of deviation by using text data. Further, for example, the display controlling function 125 may display one or more sites each having a degree of deviation equal to or larger than a predetermined level (a threshold value), by using a display mode different from display modes used for the other sites (in a highlighted manner).

The constituent elements of the apparatuses illustrated in the drawings are based on functional concepts. Thus, it is not necessary to physically configure the constituent elements as indicated in the drawings. In other words, the specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or a part of the processing functions performed in the apparatuses may be realized by a CPU and a computer program analyzed an executed by the CPU or may be realized as hardware using wired logic.

Further, with regard to the processes explained in the first embodiment, it is acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, information including various types of data and parameters that are presented in the above text and the drawings.

It is possible to realize the image processing method explained in the first embodiment by causing a computer such as a personal computer or a workstation to execute an image processing program prepared in advance. The image processing method may be distributed via a network such as the Internet. Further, the image processing method may be recorded on a computer-readable recording medium such as a hard disk, a flexible disk (FD), a Compact Disk Read-Only Memory (CD-ROM), a Magneto-Optical (MO) disk, a Digital Versatile Disk (DVD), or the like, so as to be executed as being read from the recording medium by a computer.

According to at least one aspect of the embodiments described above, it is possible to make it easy to perform the analysis related to the progress of the disease.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising:
processing circuitry configured to:
   determine a value of an index related to a predetermined disease for each of a plurality of sites included in a brain of a patient, based on a plurality of pieces of medical image data obtained by imaging the brain of the patient at each of a plurality of points in time;
   analyze, for each of the plurality of sites, a relationship between changes in the value of the index at the plurality of points in time and a progress model indicating changes in the index through progress of the predetermined disease; and
   output an analysis result obtained from the analysis for each of the plurality of sites,
   wherein the processing circuitry is further configured to
      determine the changes in the value of the index for each of the plurality of sites,
      compare speeds of the determined changes in the value of the index for each of the plurality of sites, and
      cause a display to display, in a highlighted manner, information regarding results of comparing the speeds based on the results.

2. The image processing apparatus according to claim 1, wherein the processing circuitry is further configured to cause the display to display the changes in the value of the index and the progress model so that a comparison can be made therebetween.

3. The image processing apparatus according to claim 1, wherein the processing circuitry is further configured to:
   generate a shape-modified progress model obtained by changing a shape of the progress model, by fitting the progress model to the changes in the value of the index, and
   cause the display to display the values and the shape-modified progress model so that a comparison can be made therebetween.

4. The image processing apparatus according to claim 1, wherein the processing circuitry is further configured to cause the display to display the values of the index in a radar chart in which a regular polygon is formed by lines connecting together the values of the index at the plurality of sites in progress models corresponding to a mutually-same point in time.

5. The image processing apparatus according to claim 1, wherein the processing circuitry is further configured to cause the display to display the values of the index in a radar chart in which a regular polygon is formed by lines connecting together the values of the index at the plurality of sites in normal models at a mutually-same point in time, the normal models each indicating normal changes in the value of the index caused by aging.

6. The image processing apparatus according to claim 1, wherein the processing circuitry is further configured to:
   determine values of a plurality of types of indexes,
   analyze a relationship with respect to the values of each of the plurality of types of indexes, and
   cause the display to display the changes in the value and the progress model so that a comparison can be made therebetween with respect to the values of each of the plurality of types of indexes.

7. The image processing apparatus according to claim 1, wherein the processing circuitry is further configured to:
   set a condition related to the patient,
   generate the progress model based on such one of a plurality of pieces of medical case data related to the predetermined disease that corresponds to the condition that was set, and
   analyze the relationship by using the generated progress model.

8. The image processing apparatus according to claim 1, wherein the processing circuitry is further configured to:
   determine a degree of deviation indicating a degree by which the values deviate from the progress model, and
   output the determined degree of deviation.

9. An image processing method, comprising:
   determining a value of an index related to a predetermined disease for each of a plurality of sites included in a brain of a patient, based on a plurality of pieces of medical image data obtained by imaging the brain of the patient at each of a plurality of points in time;

analyzing, for each of the plurality of sites, a relationship between changes in the value of the index at the plurality of points in time and a progress model indicating changes in the index through progress of the predetermined disease; and outputting an analysis result obtained from the analysis for each of the plurality of sites, wherein the method further comprises determining the changes in the value of the index for each of the plurality of sites, comparing speeds of the determined changes in the value of the index for each of the plurality of sites, and causing a display to display, in a highlighted manner, information regarding results of comparing the speeds based on the results.

10. A computer program product haying a non-transitory computer-readable medium including a plurality of instructions for executing image processing executable by a computer, wherein the instructions, when executed by a computer, cause the computer to perform a method comprising:

determining a value of an index related to a predetermined disease for each of a plurality of sites included in a brain of a patient, based on a plurality of pieces of medical image data obtained by imaging the brain of the patient at each of a plurality of points is time;

analyzing, for each of the plurality of sites, a relationship between changes in, the value of the index at the plurality of points in time and a progress model indicating changes to the index through progress of the predetermined disease; and outputting an analysis result obtained from the analysis for each of the plurality of sites, wherein the method further comprises determining the changes in the value of the index for each of the plurality of sites.

comparing speeds of the determined changes in the value of the index for each of the plurality of sites, and causing a display to display, in a highlighted manner, information regarding results of comparing the speeds based on the results.

* * * * *